United States Patent [19]

England

[11] 4,128,884
[45] Dec. 5, 1978

[54] METHODS AND APPARATUS FOR ANALYZING FREQUENCY DISTRIBUTIONS

[75] Inventor: John M. England, Chipperfield, England

[73] Assignee: National Research Development Corporation, London, England

[21] Appl. No.: 659,632

[22] Filed: Feb. 20, 1976

[30] Foreign Application Priority Data

Feb. 28, 1975 [GB] United Kingdom ............... 08473/75

[51] Int. Cl.² ............................................ G01N 33/16
[52] U.S. Cl. ............................... 364/416; 235/92 PC; 324/71 R; 364/555
[58] Field of Search ........... 235/151.3, 151.35, 92 PC; 324/71 R; 356/39; 23/230 R, 253 R; 364/416, 555

[56] References Cited

U.S. PATENT DOCUMENTS

| 3,700,867 | 10/1972 | Gogg | 235/151.3 |
| 3,916,176 | 10/1975 | Alien et al. | 235/151.3 |
| 3,973,189 | 8/1976 | Angel et al. | 235/151.3 X |
| 3,973,725 | 8/1976 | Watanabe et al. | 235/151.3 X |
| 4,043,756 | 8/1977 | Sommervold | 235/151.35 X |

Primary Examiner—Edward J. Wise
Attorney, Agent, or Firm—Cushman, Darby & Cushman

[57] ABSTRACT

Methods and apparatus for determining the proportion of items in a distribution having a particular characteristic where the distribution contains other items, and the various types of items form normal or log-normal sub distributions making up the overall distribution. The invention is particularly useful for determining the proportion of myeloid and lymphoid cells in a blood sample by studying the volumes of the leucocytes.

16 Claims, 5 Drawing Figures

METHODS AND APPARATUS FOR ANALYZING FREQUENCY DISTRIBUTIONS

The present invention relates to apparatus for analysing frequency distributions which include normal, or log-normal sub-distributions. The invention also relates to a method and apparatus for determining the proportion of myeloid or lymphoid cells in a prepared blood sample containing both types of cells.

Figure 1:
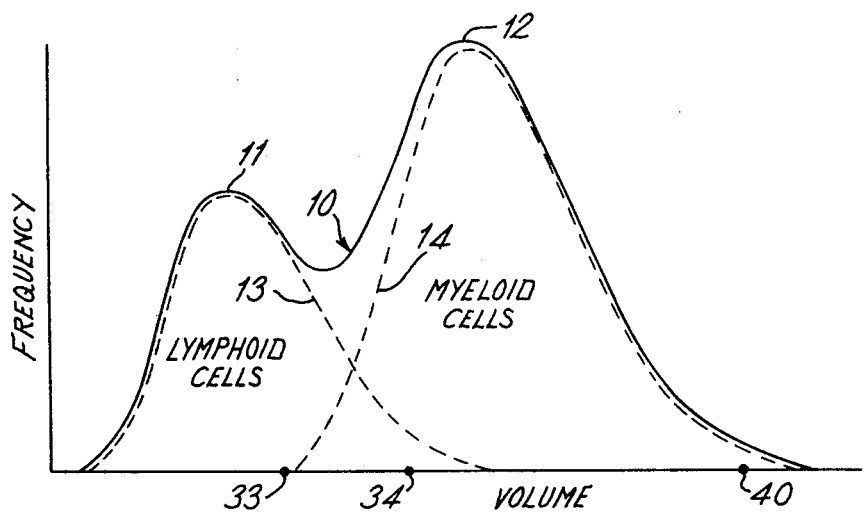

As is already known, immature and mature myeloid cells (promyelocytes, myelocytes, metamyelocytes, neutrophils, monocytes, eosinophils and basophils) are larger than lymphoid cells (lymphoblasts and lymphocytes) so that it is possible to estimate the proportion of myeloid and lymphoid cells in a blood sample by studying the volume of the leucocytes. The volume distribution for leucocytes is shown in FIG. 1 and designated 10. The distribution has two peaks 11 and 12 and the dashed curves 13 and 14 show that the overall distribution 10 is made up of two log-normal distributions due to the lymphoid and myeloid cells, respectively. The volume distribution curve is, however, difficult to analyse mathematically and reliance has previously been placed on digital computers. Unfortunately the need for a digital computer has precluded any widespread use of this method of automating the differential leucocyte count.

According to a first aspect of the present invention there is provided a method of determining the proportion of a first type of cell in a blood sample containing cells of the first type and a second type, including the steps of removing all cells except for the first type and the second type from the sample, obtaining electrical signals representative of the volumes of the remaining cells, one signal for each cell, analysing the signals to determine a distribution of cell frequency versus cell volume; and determining the value of $KM/KM + L$, for the distribution determined if it contains normal sub-distributions for the first and second cells, or for a distribution equivalent to the distribution determined but including normal sub-distributions for the first and second cells, where M and L are the peak frequencies of the first and second types of cells, respectively, and K is the ratio of the standard deviation of the first type of cell divided by the standard deviation of the second type of cell.

The fraction $KM/KM + L$ arises because for normal distributions the number of cells under a distribution is proportional to the peak frequency of the distribution divided by its standard deviation.

The first and second types of cells may be myeloid and lymphoid cells, respectively, or vice versa.

The advantage of the method according to the invention is that the value of $KM/KM + L$ can be determined easily, for example by means of equipment specifically designed for that purpose, without the need for a digital computer. Thus the method can be automated economically.

However, before the method of the invention can be put into practice a sample blood smear must be observed to determine whether the sample contains an increased number of lymphoid and myeloid cells due to leukaemia and whether the myeloid cells include eosinophils. If so the method of the invention is probably not relevant since the proportions of lymphoid and myeloid cells is no longer main point of interest. Normal practice, however, usually includes microscopic inspection of a blood smear before the proportion of myeloid or lymphoid cells is determined.

Where sub-distributions of myeloid and lymphoid cells making up the overall distribution are each log-normal distributions, then one of three different ways of carrying out the analysis of signals and finding the value of $KM/KM + L$ may be used:

Firstly, the frequency of cells is found in linearly divided volume intervals, the linear volume axis of the distribution is then considered as divided on a logarithmic scale, and lastly the value of $KM/KM + L$ is calculated but with the distribution treated as having linearly divided volume intervals each of which corresponds to one of the logarithmic intervals.

Secondly, the logarithms of the volume signals are determined and then the frequency in linearly divided intervals is found; and Thirdly, the analysis is carried out to provide not only the frequencies of the cells within linearly divided volume intervals but also volume signals, each of which is associated with one of the intervals and is representative of the mean volume in that interval.

In the first and second methods, the log-normal sub-distributions are converted to normal distributions either in the first case by taking the frequency of cells in volume intervals calculated in the way described, or in the second case by determining the logarithms of the volume signals before finding the frequency in linear intervals. Thus in the first and second cases peak values corresponding to L and M are found.

If the third method of analysis is used M, L and K are replaced by M', L' and K' as is now explained.

For a log-normal frequency distribution the maximum value of the product: frequency in a linearly divided interval multiplied by mean volume of that interval, is proportional to the number of cells under the distribution divided by the standard deviation of the logarithms of the volumes of the cells. The proportions of different types of cells can thus be calculated and in doing so for the general case a fraction $K'M'/K'M' + L'$ is derived; where K' is the ratio of the standard deviation of the logarithms of the volumes of the myeloid cells divided by the standard deviation of the logarithms of the volumes of the lymphoid cells; M' is the peak of the product: frequency of myeloid cells in a volume interval multiplied by mean volume for that interval; and L' is the peak of the product: frequency of lymphoid cells in a volume interval multiplied by mean volume for that interval. Carrying out this derivation is equivalent to converting the log-normal sub-distributions to normal distributions having "log volumes" versus "volume times frequency". Having made this conversion peak "volume times frequency" values L' and M' are found and $K'M'/K'M' + L'$ is determined. It can thus be seen that $K'M'/K'M' + L$ is equivalent to $KM/KM + L$ for the normal sub-distributions which would be obtained if the above mentioned conversion were in fact carried out.

Where the method of preparation of the myeloid and lymphoid cells results in sub-distributions which are normal distributions, then the analysis of signals representing cell volume may be carried out by determining the frequency of cells within linearly divided volume intervals.

As can be seen in FIG. 1 the sub-distributions for the two types of cells overlap and it is therefore preferable to correct the fraction $KM/KM + L$ to allow for this overlap.

According to a second aspect of the present invention there is provided apparatus for determining the proportion of items in the $s^{th}$ one of a number of log-normal sub-distributions in an overall distribution containing p such sub-distributions, the distribution being frequency of items versus values of a characteristic, the apparatus including calculating means for providing an output signal representative of $$\sigma_s N_s / \sum_{n=1}^{n=p} \sigma_n \hat{N}_n$$

where $N_n$ is the peak value of the product: frequency within an interval multiplied by a number representative of the mean value of the characteristic in that interval, the intervals being divided linearly along that axis of the distribution which is representative of the characteristic, and $\sigma_n$ being the standard deviation of the logarithms of the values of the characteristic for items in the $n^{th}$ sub-distribution.

Preferably the apparatus includes means for adjusting the output signal to allow for any overlap between the sub-distributions.

Where proportions of cells in the leucocyte distribution are to be determined the characteristic is, of course, the volumes of the cells; and the output signal is representative of K'M'/K'M' + L' where K', M' and L' have the meanings previously given.

For determining the proportions of lymphoid or myeloid cells the apparatus may also include a counter for processing blood samples and providing a signal for each cell representative of the volume of that cell, and an analyser for determining the frequency of cells within each of a number of volume intervals. The analyser then provides two signals one representative of frequency within an interval and the other representative of the mean volume of the interval, these signals being supplied to the calculating means.

According to a third aspect of the present invention there is provided apparatus for determining the proportion of items in the $r^{th}$ one of a number of normal sub-distributions in a distribution containing p such sub-distributions, the overall distribution being frequency of items versus values of a characteristic, the apparatus including calculating means for providing an output signal representative of $$\sigma_s N_s / \sum_{n=1}^{n=p} \sigma_n \hat{N}_n,$$

where $M_n$ is the peak value of frequency in linearly divided intervals of the value of a characteristic and $\sigma_n$ is the standard deviation of the $n^{th}$ sub-distribution.

Again, where this apparatus is applied to determining the proportions of different types of cell in a leucocyte volume distribution, the characteristic is cell volume and with only two types of cells the output signal becomes representative of KM/KM + L. However since the sub-distributions are now normal distributions M and L are simply peak frequencies.

If a blood sample is prepared in such a way that the myeloid and lymphoid cells form normal sub-distributions, then the apparatus according to the third aspect of the invention may include means for providing a signal for each cell and representative of the volume of that cell, and means for analysing the signals so provided to determine the frequency of cells within linearly divided volume intervals, the output of the analyser being coupled to the calculating means.

However where the cells are prepared in a more conventional way which results in log-normal sub-distribution, apparatus according to the third aspect of the invention may include means for providing signals representative of cell volumes. The apparatus may then also include either: an analyser providing frequencies of cells in volume intervals calculated by considering the linear volume axis of the distribution as divided on a logarithmic scale and making the intervals numerically equal on this log scale; or means for determining log volume signals representative of the logarithms of the cell volume signals, and analyser means for determining the frequency of cells in equally divided intervals. In both these alternative apparatuses the output signals from the analyser means are passed to the calculating means since by dividing the log scale in intervals calculated as described or by taking logarithms of the signals representative of cell volumes, the log-normal sub-distributions are converted to normal sub-distributions.

Again means for correcting the output from the calculating means are preferably provided to allow for any overlap between sub-distributions.

Figure 2:
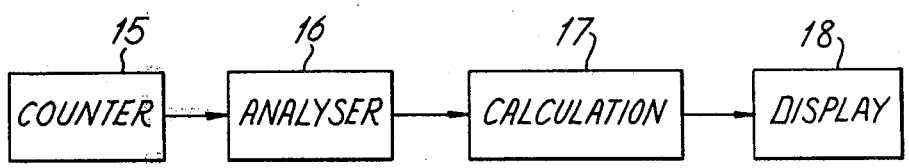
Figure 3:
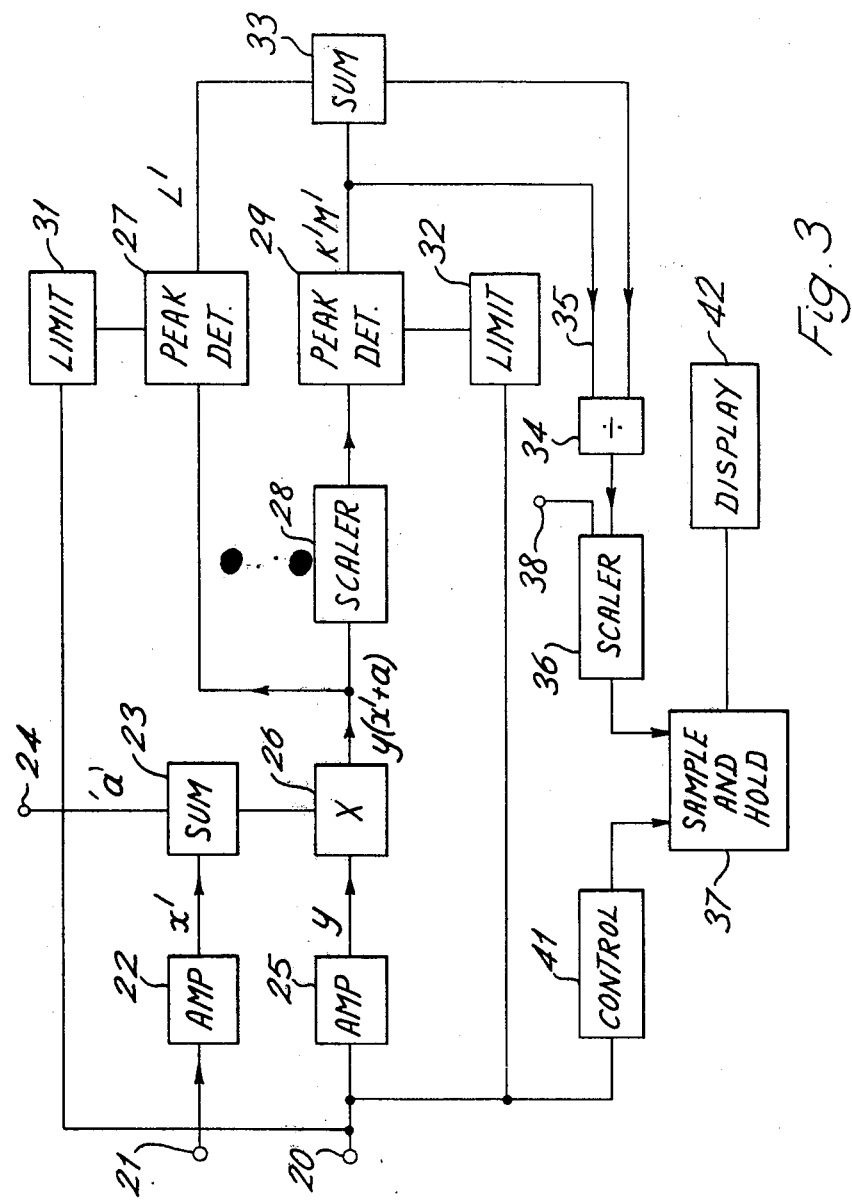
Figure 4:
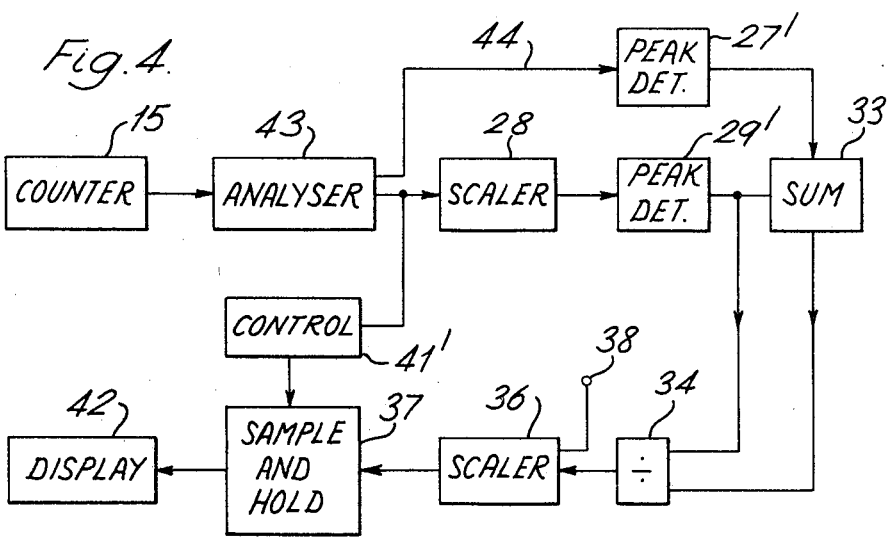
Figure 5:
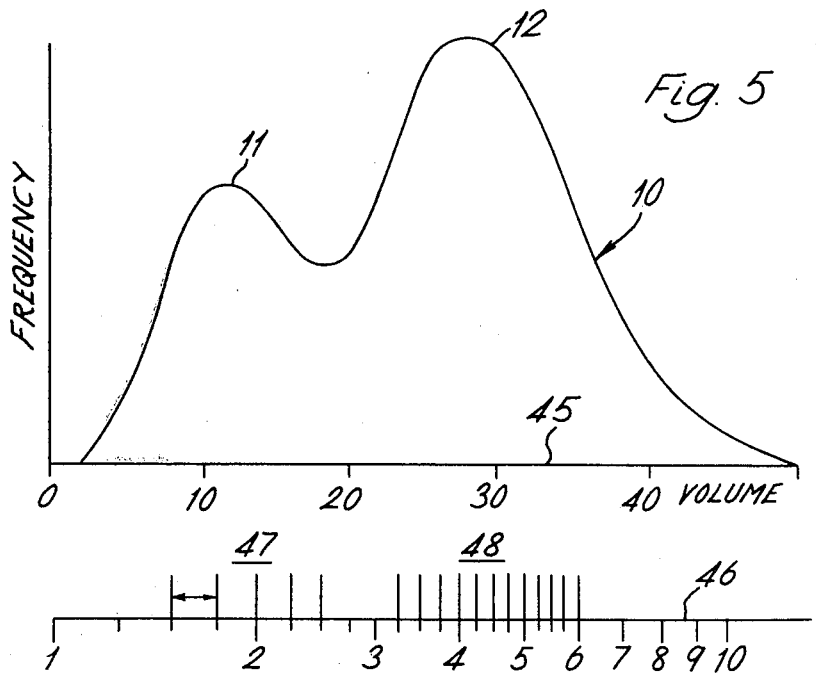

Certain embodiments of the invention will now be described, by way of example, with reference to the accompanying drawings in which:

FIG. 1 shows the leucocyte volume distribution curve,

FIG. 2 is a block diagram including apparatus according to the invention for determining the proportion of lymphoid or myeloid cells in a prepared blood sample, FIG. 3 is a block diagram of part of the apparatus of FIG. 2, FIG. 4 is a block diagram of a further apparatus according to the invention for determining the proportion of myeloid or lymphoid cells in a prepared blood sample, and FIG. 5 is a graph showing channel ranges for the analyser of FIG. 4.

Before analysing a blood sample to obtain the leucocyte volume distribution it is necessary to remove red cells and this may be carried out in the way described in the paper 'Differential White Cell Counts by Frequency Distribution Analysis of Cell Volumes' by N. C. Hughes-Jones, Ian Norley, Janet M. S. Young and J. M. England, in J. Clin. Path., 1974, 27, pages 623 to 625. The remaining leucocyte cells after removal of the red cells are counted in a counter 15 (see FIG. 2) which provides a pulse for every cell counted, the height of the pulse being proportional to the cell volume. The output of the counter 15 is connected to an analyser 16 which provides a series of signals each representative of the number of cells having volumes within a certain equal volume interval or channels, and a signal representative of the mean value of the interval. A suitable counter is made by Coulter Electronics and the analyser may be a Coulter Electronics Channelyzer having controls to set the width of each 'channel', and an output, provided primarily for a plotter, indicating the channel number and thus representative of the mean value of the voltage interval corresponding to that channel. In addition of course the channelyzer also provides another output giving the frequency of cells within each interval.

A circuit 17 which receives the outputs from the analyser calculates the fraction K'M'/K'M' + L' and passes a signal to a display 18 which at the end of each blood-sample scan provides a display giving the value of the above mentioned fraction.

The circuit 17 and the display 18 are shown in more detail in FIG. 3. Here the outputs from the analyser 16 are applied to terminals 20 and 21, the terminal 20 being the frequency input while the terminal 21 receives a ramp voltage corresponding to channel number. The voltage applied to the terminal 21 is passed through a type 741 operational amplifier 22 and on to a summing circuit 23 again based on a type 741 operational amplifier. In the summing circuit 23 a voltage applied to a terminal 24 and representative of the value of cell volume at the lower end of the lowest channel is added to the output from the amplifier 22.

Signals applied to the terminal 20 are passed through a type 741 operational amplifier 25 before reaching an analogue multiplier circuit 26 which also receives the sum signal from the circuit 23. Thus the output from the multiplier circuit 23 is $y(x' + a)$ where y represents frequency, $x'$ represents the ramp voltage from the analyser and 'a' represents the volume at the lower end of the lowest analyser channel. A suitable multiplier for the circuit 26 is the Analog Devices type AD 503 L.

The output from the multiplier 26 is branched to a first peak detector 27 for detecting the lymphoid cell frequency peak 11 (see FIG. 1), and by way of a scaler circuit 28 to a second peak detector circuit 29 for detecting the myeloid cell frequency peak 12. The scaler 28 may be a type 741 operational amplifier with a variable feed-back resistor. The setting of this resistor is dependent on the value of $K'$ and is discussed in more detail below.

In order to detect first the peak 11 and then the peak 12, the voltage ramp signal x applied at the terminal 21 is used to operate two limit circuits 31 and 32. When x increases to a value corresponding to volume at point 33 in FIG. 1 the limit circuit 31 operates preventing further signals from reaching the peak detector circuit 27. Thus the output signal of the circuit 27 is $L'$ corresponding to the peak 11. When the value of x increases further until it reaches a value corresponding to the point 34 in FIG. 1, the limit circuit 32 operates connecting the peak detector 29 to the circuit 28 for the first time. Thus the circuit 29 provides a signal representative of the value $K'M'$, corresponding to the peak 12 in FIG. 1.

A further type 741 operational amplifier connected as a summing circuit 33 adds the signals representative of $K'M'$ and $L'$ and passes them to a division circuit 34 which also receives the signal representative of $K'M'$ by way of a channel 35. The division circuit 34 may also be an Analog Devices type AD 530 L circuit connected this time to divide the signal in the channel 35 by the output signal from the circuit 33.

From the division circuit 34 the signal passes through a further type 741 operational amplifier connected as a scaler circuit 36 before reaching a sample-and-hold circuit 37. The scaler circuit 36 multiplies the output signal from the division circuit 34 and adds an offset voltage applied at a terminal 38, thus making two corrections necessary in allowing for the overlap of the two distributions 13 and 14 in FIG. 1. The setting of this scaler is described in more detail below.

As the value of the voltage applied at the terminal 21 reaches a point somewhere in the region designated 40 in FIG. 1, a control circuit 41 operates causing the sample-and-hold circuit 37 to sample the output of the scaler 36 and cause it to be displayed in a digital voltmeter display 42. Thus the value of $K'M'/K'M' + L'$ is displayed.

The value of $K'$ is best calculated for a number of typical blood samples and then set upon the potentiometer which forms the feedback resistor in the operational amplifier of the scaler 28. In order to set up the scaler 36, a graph is plotted of proportion displayed, that is by the display 42, against actual proportion as calculated by other means. In general a straight line will then be obtained which is offset from the graph origin and at a gradient other than 45°. Clearly, for equal scale axes the straight line should go through the origin at 45°. Hence from the graph obtained an offset voltage, to be applied to the terminal 38, can be calculated which, in effect, moves the curve to the origin. The multiplicand for the scaler 36 is set using a potentiometer in a feedback loop for the operational amplifier of the scaler. This potentiometer is set to correct the gradient of the graph so that it becomes 45°.

Another arrangement for determining the proportion of myeloid cells in a blood sample prepared in the same way as mentioned above is shown in FIG. 4. The counter 15 is as described in connection with FIG. 2 but an analyser 43 replaces the analyser 16. The analyser 43 provides the frequencies of cells in channels (that is volume ranges) divided as shown on the lower scale in FIG. 5 where the leucocyte volume distribution 10 is again shown. FIG. 5 has two horizontal axes 45 and 46 divided with a linear scale and a logarithmic scale, respectively, the units shown being arbitrary. In a group of channels 47 positioned under the lymphoid peak 11 each channel has a range 0.25 units on the log scale and similarly in a group of channels 48 positioned under the myeloid peak 12 each channel again has a range of 0.25 units. This arrangement of channels in effect re-arranges the two log-normal sub-distributions as normal sub-distributions; thus if the distributions were drawn again with the frequencies within the groups of channels 47 and 48 plotted on a linear volume scale normal sub-distributions would be obtained.

Instead of the one hundred or so channels of the Coulter channelyzer the analyser 43 has fifteen channels four in the region of the lymphoid cell peak 11 and eleven in the region of the myeloid cell peak 12. Other numbers of channels could, of course, be employed. The output signals from the channels 47 are passed to a peak detector 27' while those from the channels 48 are taken to a peak detector 29'. From this point the circuit of FIG. 4 is the same as that of FIG. 3 except that a control circuit 41' is operated on receipt of the output signal from the highest channel of the analyser 43, so that the display is given when the blood sample scan is complete. With the arrangement of FIG. 4 KM/KM + L is displayed.

An alternative form of analyser may be used which again uses channels divided in the way shown in FIG. 5, but provides digital output signals instead of analog signals. The calculation of KM/KM + L is then carried out by digital circuits. Such an arrangement is not further described here since its implementation will be clear to those familiar with such circuits. Digital circuits may be used with the analyser 43 of FIG. 4 if its two output terminals are each passed to an analogue-to-digital converter.

It will be apparent that the invention may be put into practice in many other ways, for example by using other arrangements of circuits to determine KM/KM + L or $K'M'/K'M' + L'$.

I claim:

1. A method of determining the proportion of a first type of cell in a blood sample containing cells of the first type and a second type, including the steps of:
    removing all cells except for the first type and the second type from the sample,
    generating electrical count signals representative of the volume of the remaining cells, one signal for each cell,
    generating, from said count signals, distribution signals indicative of a distribution of cell frequency versus cell volume, and
    generating from said distribution signal a proportion signal indicative of the value of KM/KM + L, for a distribution representative of said first mentioned distribution and containing normal sub-distributions for the first and second cells, where M and L are the peak frequencies of the first and second types of cells, respectively, and K is the ratio of the standard deviation of the volume of the first type of cell divided by the standard deviation of the volume of the second type of cell.

2. A method according to claim 1 wherein in generating said proportion signal indicative of the value of KM/KM + L, an allowance is made for any overlap of the two sub-distributions.

3. A method according to claim 2 for use where the distribution of cell frequency versus cell volume contains two log-normal sub-distributions when the volumes are divided linearly, wherein in said generating distribution signals step, logarithmic volume division is substituted for linear division without recalculating frequency values, and the value of KM/KM + L is determined with the distribution treated as having new linearly divided volume intervals, each of which corresponds to a respective one of the logarithmic intervals.

4. A method according to claim 2 for use where the distribution of cell frequency versus cell volume contains two log-normal sub-distributions when the volumes are divided linearly, wherein said generation of distribution step includes the step of generating signals indicative of the logarithms of the count signals, and in generating said proportion signals step, the value of KM/KM + L is determined for a distribution in which the frequency of the logarithmic signals is given for linearly divided intervals.

5. A method according to claim 2 wherein the method is for finding the proportions of myeloid or lymphoid cells and the first and second types of cell are myeloid or lymphoid cells, respectively, or vice versa.

6. Apparatus for determining the proportion of items in the $s^{th}$ one of a number of log-normal sub-distributions in an overall distribution containing p such sub-distributions, the distribution being frequency of items versus values of a characteristic, the apparatus including:
    means for generating a $N_s$ signal indicative of the peak value of the product $N_s$, such product $N_s$ being equal to the frequency in the $s^{th}$ sub-distribution within an interval multiplied by a number representative of the mean value of the characteristic in that interval; and
    means responsive to said $N_s$ signal for generating a $\sigma_s N_s$ signal indicative of the product of $N_s$ multiplied by a number $\sigma_s$; $\sigma_s$ being the standard deviation of the logarithm of the values of the characteristic for items in the $s^{th}$ sub-distribution; and
    means, responsive to said $\sigma_s N_s$ signal, for providing an output signal representative of $$\sigma_s N_s / \sum_{n=1}^{n=p} \sigma_n N_n$$

where $N_n$ is the peak value of the product of the frequency in the $n^{th}$ sub-distribution within an interval multiplied by a number representative of the mean value of the characteristic in that interval, said intervals being divided linearly along that axis of the distribution which is representative of the characteristic, and $\sigma_n$ being the standard deviation of the logarithms of the values of the characteristic for items in the $n^{th}$ sub-distribution.

7. Apparatus according to claim 6 including means for allowing for any overlap between the sub-distributions in providing a final output signal for the apparatus.

8. Apparatus for determining the proportion of items in the $r^{th}$ one of a number of normal sub-distributions in a distribution containing p such sub-distributions, the overall distributions being frequency of items versus values of a characteristic, the apparatus including:
    first means for providing a $M_r$ signal indicative of the peak value $M_r$ in the $r^{th}$ sub-distribution of frequency in linearly divided intervals of the value of a characteristic;
    second means responsive to said $M_r$ signal for generating and; a$\sigma_r M_r$ signal indicative of $M_r$ multiplied by $\sigma_r$ which is the standard deviation of the $r^{th}$ sub-distribution
    means responsive to said $\sigma_r M_r$ signal for providing an output signal representative of $$\sigma_r M_r / \sum_{n=1}^{n=p} \sigma_n M_n,$$

where $M_n$ is the peak value in the $n^{th}$ sub-distribution of frequency in linearly divided intervals of the value of a characteristic and $\sigma_n$ is the standard deviation of the $n^{th}$ sub-distribution.

9. Apparatus according to claim 8 including means for allowing for any overlap between the sub-distributions in providing a final output signal for the apparatus.

10. Apparatus for determining the proportion of a first type of cell in a blood sample containing cells of the first type and a second type, when the sample has been prepared in such a way that the volumes of the two types of cells form log-normal sub-distributions in a distribution of cell frequency versus cell volume including a counter for processing blood samples and providing a signal for each cell representative of the volume of that cell, and an analyser for determining the frequency of cells within each of a number of linearly divided volume intervals, the analyser providing, in operation, two signals one representative of frequency within an interval and the other representative of mean volume of the interval, calculating means, coupled to receive the said two signals, for providing an output signal representative of K'M'/K'M' + L' where K' is the ratio of the standard deviation of the logarithms of volumes of the first type of cells divided by the standard deviation of the logarithms of the volumes of the second type of cells; M' is the peak of the product frequency of the first type of cells in a volume interval multiplied by mean volume for that interval and L' is the peak of the product frequency of second type of cells in a volume interval multiplied by mean volume for that interval, and means for allowing for any overlap between the sub-distributions in providing a final output signal for the apparatus.

11. Apparatus according to claim 10 wherein the calculating means includes means for adjusting the signal which is representative of mean volume to be directly proportional to mean volume, multiplier means for multiplying the adjusted signal by the signal representative of frequency to provide a product signal, a first scaler circuit for multiplying the product signal by a quantity representative of the ratio of the standard deviation of the logarithms of the volumes of the cells of the first type divided by the standard deviation of the logarithms of the volumes of the cells of the second type, means for providing first and second peak signals for the product signal within a predetermined lower volume-interval range, and for the output signal of the first scaler circuit within a predetermined upper volume-interval range, respectively, means for summing the first and second peak signals to provide a sum signal and means for dividing the second peak signal by the sum signal to provide the said output signal of the calculating means, and wherein the means for adjusting the calculating-means output signal is a second scaler circuit coupled at the output of the calculating means.

12. Apparatus for determining the proportion of a first type of cell in a blood sample containing cells of the first type and a second type, when the sample has been prepared in such a way that the volumes of the two types of cells form normal sub-distributions in a distribution of cell frequency versus cell volume, the apparatus including means for providing a signal for each cell and representative of the volume of that cell, and means for analysing the signals so provided to determine the frequency of cells within linearly divided volume intervals, calculating means coupled to the output of the analyser means, for providing an output signal representative of KM/KM + L where M and L are in the peak frequencies of the first and second types of cells, respectively, and K is the ratio of the standard deviation of the volume of the first type of cell divided by the standard deviation of the volume of the second type of cell, and means for allowing for any overlap between the sub-distributions in providing a final output signal for the apparatus.

13. Apparatus for determining the proportion of a first type of cell in a blood sample containing cells of the first type and a second type, when the sample has been prepared in such a way that the volumes of the two types of cells form log-normal sub-distributions in a distribution of cell frequency versus cell volume, the apparatus including means for providing a signal for each cell and representative of the volume of that cell, and means for analysing the signals so provided to determine the frequency of cells within logarithmically divided volume intervals, calculating means coupled to the output of the analyser means, for providing an output signal representative of KM/KM + L where M and L are the peak frequencies of the volumes in the logarithmically divided intervals of the first and second types of cells, respectively, and K is the ratio of the standard deviation of the volume of the first type of cell measured in the logarithmically divided intervals divided by the standard deviation of the second type of cell also measured in the logarithmically divided intervals, and means for allowing for any overlap between the sub-distributions in providing a final output signal for the apparatus.

14. Apparatus according to claim 13 wherein the analyser means provides first and second signals representative of volume interval and frequency, respectively, and the calculating means includes a first scaler circuit for multiplying the first signal by a quantity representative of the ratio of the standard deviation of the volumes of the cells of the first type, divided by the standard deviation of the volumes of the cells of the second type determined with the logarithmically divided intervals treated as linearly divided intervals, means for providing first and second peak signals for the first signal within a predetermined lower interval range, and for the output signal of the first scaler circuit within a predetermined upper interval range, respectively, means for summing the first and second peak signals to provide a sum signal and means for dividing the second peak signal by the sum signal to provide the said output signal of the calculating means, and wherein the means for adjusting the calculating means output signal is a second scaler circuit coupled at the output of the calculating means.

15. Apparatus for determining the proportion of a first type of cell in a blood sample containing cells of the first type and a second type, the sample being prepared in such a way that the volumes of the two types of cells form log-normal sub-distributions in a distribution of cell frequency versus cell volumes, the apparatus including means for providing a signal for each cell and representative of the volume of that cell, means for determining log-volume signals representativ of the logarithms of the cell volume signals, analyser means for determining the frequency of the log-volume signals in equally divided intervals, calculating means, coupled to the output of the analyser means, for providing an output signal representative of KM/KM + L where M and L are the peak frequencies of the log-volumes of the first and second types of cells, respectively, and K is the ratio of the standard deviation of the logarithms of the first type of cell divided by the standard deviation of the logarithms of the second type of cell, and means for allowing for any overlap between the sub-distributions in providing a final output signal for the apparatus.

16. A method of determining the proportion of a first type of cell in a blood sample containing cells of the first type and a second type, including the steps of:
generating electrical count signals representative of the volume of the remaining cells, one signal for each cell;
generating, from said count signals, distribution signals indicative of a distribution of cell frequency versus cell volume, said distribution of cell frequency versus cell volume containing two log-normal sub-distributions when the volumes are divided linearly,
generating a signal representative of the value K'M'/K'M' + L' where K' is the ratio of the standard deviation of the logarithms of the volumes of the first type of cell divided by the standard deviation of the logarithms of the volumes of the second type of cells; M' is the peak of the product of frequency of the first type of cells in a volume interval multiplied by mean volume for that interval; and L' is the peak of the product of frequency of the second type of cells in a volume interval multiplied by mean volume for that interval.

* * * * *

UNITED STATES PATENT AND TRADEMARK OFFICE
CERTIFICATE OF CORRECTION

PATENT NO. : 4,128,884

DATED : December 5, 1978

INVENTOR(S) : JOHN M. ENGLAND

It is certified that error appears in the above-identified patent and that said Letters Patent are hereby corrected as shown below:

Col. 1, lines 39-40, delete the following:

"for the distribution determined if it contains normal sub-distributions for the first and second cells, or"

Col. 2, lines 59-64, delete in entirety.

Col. 3, line 57, after "volume" insert -- . --.

Col. 3, lines 58-61, delete in entirety.

Col. 3, line 62, change "is" to -- can be --.

Col. 4, lines 4-5, change to read:

"conventional way a log-normal sub-distribution results. Thus, apparatus according to the third aspect of the"

Claim 12, delete in entirety.

UNITED STATES PATENT AND TRADEMARK OFFICE
CERTIFICATE OF CORRECTION

PATENT NO. : 4,128,884

DATED : December 5, 1978

INVENTOR(S) : JOHN M. ENGLAND

It is certified that error appears in the above-identified patent and that said Letters Patent are hereby corrected as shown below:

Claim 13, line 66, after "the" (second occurrence) insert -- volume of the --.

Claim 15, line 32, correct the spelling of "representative".

Claim 16, line 49, change "remaining" to -- first and second type --.

Claim 16, line 50, after "each" insert -- such --.

Signed and Sealed this

Twenty-second Day of May 1979

[SEAL]

Attest:

RUTH C. MASON
Attesting Officer

DONALD W. BANNER
Commissioner of Patents and Trademarks